United States Patent [19]
Bjorkquist et al.

[11] Patent Number: 6,127,593
[45] Date of Patent: Oct. 3, 2000

[54] FLUSHABLE FIBROUS STRUCTURES

[75] Inventors: David William Bjorkquist, Wyoming; Todd Leon Mansfield, Cincinnati, both of Ohio

[73] Assignee: The Procter & Gamble Company, Cincinnati, Ohio

[21] Appl. No.: 08/976,746

[22] Filed: Nov. 25, 1997

[51] Int. Cl.⁷ .................................................. A61F 13/20
[52] U.S. Cl. ........................ 604/364; 604/372; 604/374; 604/376; 604/367; 525/54.3; 525/61; 442/119; 428/475.8; 428/913
[58] Field of Search ................................. 604/364, 367, 604/365, 370, 372, 374, 375, 376, 377; 525/54.3, 61; 442/119; 428/475.8, 511, 913

[56] References Cited

U.S. PATENT DOCUMENTS

| | | | |
|---|---|---|---|
| 3,645,928 | 2/1972 | Wakamura et al. | 260/2.5 |
| 3,692,725 | 9/1972 | Duchane | 260/29.6 |
| 3,923,592 | 12/1975 | George et al. | 162/168 |
| 4,002,796 | 1/1977 | Baldi et al. | 428/375 |
| 4,242,408 | 12/1980 | Evani et al. | 428/290 |
| 4,258,849 | 3/1981 | Miller | 206/812 |
| 4,833,301 | 5/1989 | Furtek | 219/388 |
| 5,110,390 | 5/1992 | Martini et al. | 156/244.11 |
| 5,281,306 | 1/1994 | Kakiuchi et al. | 162/158 |
| 5,384,189 | 1/1995 | Kuroda et al. | 428/288 |
| 5,393,602 | 2/1995 | Urry | 428/290 |
| 5,415,643 | 5/1995 | Kolb | 604/367 |
| 5,466,518 | 11/1995 | Isaac et al. | 428/288 |
| 5,476,457 | 12/1995 | Roessler et al. | 604/364 |
| 5,496,874 | 3/1996 | Faass et al. | 524/56 |
| 5,500,068 | 3/1996 | Srinivasan et al. | 156/148 |
| 5,500,281 | 3/1996 | Srinivasan et al. | 428/288 |
| 5,509,913 | 4/1996 | Yeo | 604/364 |
| 5,656,746 | 8/1997 | Smith et al. | 536/63 |
| 5,690,790 | 11/1997 | Headlam et al. | 162/175 |
| 5,698,688 | 12/1997 | Smith et al. | 536/56 |

FOREIGN PATENT DOCUMENTS

| | | | |
|---|---|---|---|
| 0 372 388 B1 | 6/1990 | European Pat. Off. | D21H 17/43 |
| 0 582 123 A1 | 2/1994 | European Pat. Off. | |
| 0 639 381 A1 | 2/1995 | European Pat. Off. | A61L 15/62 |
| 0 768 425 A2 | 4/1997 | European Pat. Off. | D21H 21/20 |
| 07222768A | 8/1995 | Japan . | |
| 8-1348 | 1/1996 | Japan | D04H 1/42 |
| 8-19571 | 1/1996 | Japan | A61F 13/15 |
| 9-164096 | 6/1997 | Japan | A47K 10/16 |
| 9-217293 | 8/1997 | Japan | D21H 10/16 |
| 1 451 619 | 12/1973 | United Kingdom . | |
| WO 95/16474 | 6/1995 | WIPO | A61L 15/62 |

OTHER PUBLICATIONS

Chemical Abstract #127, 43–Cellulose, Lignin, Paper, and Other Wood Products, vol. 127, No. 8, p. 746 (1997).

*Primary Examiner*—Mark O. Polutta
*Attorney, Agent, or Firm*—Carl J. Roof; Julia A. Glazer; Don E. Hasse

[57] ABSTRACT

The present invention relates to a flushable fibrous structure that is particularly useful as a disposable tissue product and as a component (e.g., topsheets) for absorbent articles such as catamenial pads, diapers, incontinent articles and the like. The invention specifically relates to a flushable fibrous structure that has an in-use wet tensile strength of at least about 100 g/in. and a disposal wet tensile strength of not more than about 30 g/in. The invention also relates to absorbent articles comprising the fibrous structures, and methods for making the structures.

36 Claims, 1 Drawing Sheet

FLUSHABLE FIBROUS STRUCTURES

FIELD OF THE INVENTION

The present invention relates to flushable fibrous structures. These fibrous structures may be in the form of either paper or synthetic nonwovens.

BACKGROUND OF THE INVENTION

Wet strength is a desirable attribute of many disposable paper products, that must maintain their integrity for an extended period of time when wetted during their intended use. Such products include toilet and facial tissue, paper towels, and some of the components of diapers and adult incontinents, feminine hygiene products such as sanitary napkins, pantiliners and tampons, and the like.

A number of resins have been used or disclosed as being useful for providing wet strength to paper products and components thereof. Certain of these wet strength additives have resulted in paper products with permanent wet strength, i.e., paper which when placed in an aqueous medium retains a substantial portion of its initial wet strength over time. Exemplary resins of this type include urea-formaldehyde resins, melamine-formaldehyde resins and polyamide-epichlorohydrin resins. Such resins exhibit limited wet strength decay, even in the presence of excess water.

However, permanent wet strength in paper products is often an unnecessary and undesirable property. Indeed, due to the permanent wet strength of such products, or components thereof, paper products are generally disposed of after brief periods of use into landfill, incinerators, etc. Such products can therefore pose a significant burden on the solid waste stream. The desirable alternative of directing used paper products to municipal sewage treatment facilities or private septic systems is typically obviated by the inclusion of "unflushable" components, such as topsheets and backsheets. That is, clogging of these systems can result if the product, or one or more of its components, permanently retains hydrolysis-resistant strength properties. Therefore, efforts have been undertaken to provide paper product components, and specifically incontinent and personal hygiene product components, that have sufficient wet integrity when wetted with aqueous body fluids during use, but which lose their integrity when exposed to large amounts of waste water (such as is encountered in a typical toilet) such that they traverse plumbing and disintegrate in municipal/septic systems. Numerous approaches for providing paper products claimed as having good initial wet strength which decays significantly over time have been suggested. For example, various approaches suggested to achieve temporary wet strength are described in U.S. Pat. No. 3,556,932, Coscia et al., issued Jan. 19, 1971; U.S. Pat. No. 3,740,391, Williams et al., issued Jun. 19, 1973; U.S. Pat. No. 4,258,849, Miller, issued Mar. 31, 1981; U.S. Pat. No. 3,096,228, Day et al., issued Jul. 2, 1983; U.S. Pat. No. 4,605,702, Guerro et al., issued Aug. 12, 1986; U.S. Pat. No. 4,675,394, Solarek, et al., issued Jun. 23, 1987; U.S. Pat. No. 5,509,913, issued Apr. 23, 1996 to Yeo; U.S. Pat. No. 4,603,176, Bjorkquist et al., issued Jul. 29. 1986; U.S. Pat. No. 4,981,557, Bjorkquist, issued Jan. 1, 1991; and U.S. Pat. No. 5,138,002, Bjorkquist, issued Aug. 11, 1992.

While the art has provided a variety of synthetic nonwoven products having varying degrees of wet strength, none has provided paper products that exhibit the combined in-use wet integrity and disposal decay properties of the present structures. In particular, existing temporary wet strength products exhibit immediate and rapid tensile decay upon exposure to aqueous fluids. Obviously, rapid decay in the presence of body fluids renders these materials unsuitable for use in absorbent articles which must retain their strength up until the time of disposal. Conversely, as discussed above, those paper products possessing more permanent wet strength will not decay even when exposed to large quantities of aqueous liquids.

It is therefore an object of this invention to provide flushable fibrous structures in the form of either paper-based or synthetic nonwovens that provide initial tensile strength even when subjected to aqueous body fluids, but which decay rapidly in the presence of excess amounts of water encountered during disposal. These structures may be in the form of a paper product such as toilet tissue, facial tissue, tissue towels and the like, or they may be used as a component in personal products, such as absorbent article topsheets, backsheets and the like.

SUMMARY OF THE INVENTION

The present invention relates to flushable fibrous structures having an in-use wet tensile strength of at least about 100 g/in, and a disposal wet tensile strength of not more than about 30 g/in. The invention specifically relates to flushable fibrous structures comprising a binder which comprises a polymer and a salt to provide the desired in-use and disposal wet strength characteristics. The polymer, when used in conjunction with the salt, is relatively insoluble in aqueous fluids encountered in use, but is soluble in the presence of excess water, such at that encountered in a typical sanitary disposal system. The invention further relates to products consisting of (e.g., tissue products such as facial and toilet tissue) or comprising (e.g., absorbent articles) the flushable fibrous structures, as well as methods for making the fibrous structures.

DETAILED DESCRIPTION OF THE INVENTION

I. Definitions

Figure 1:
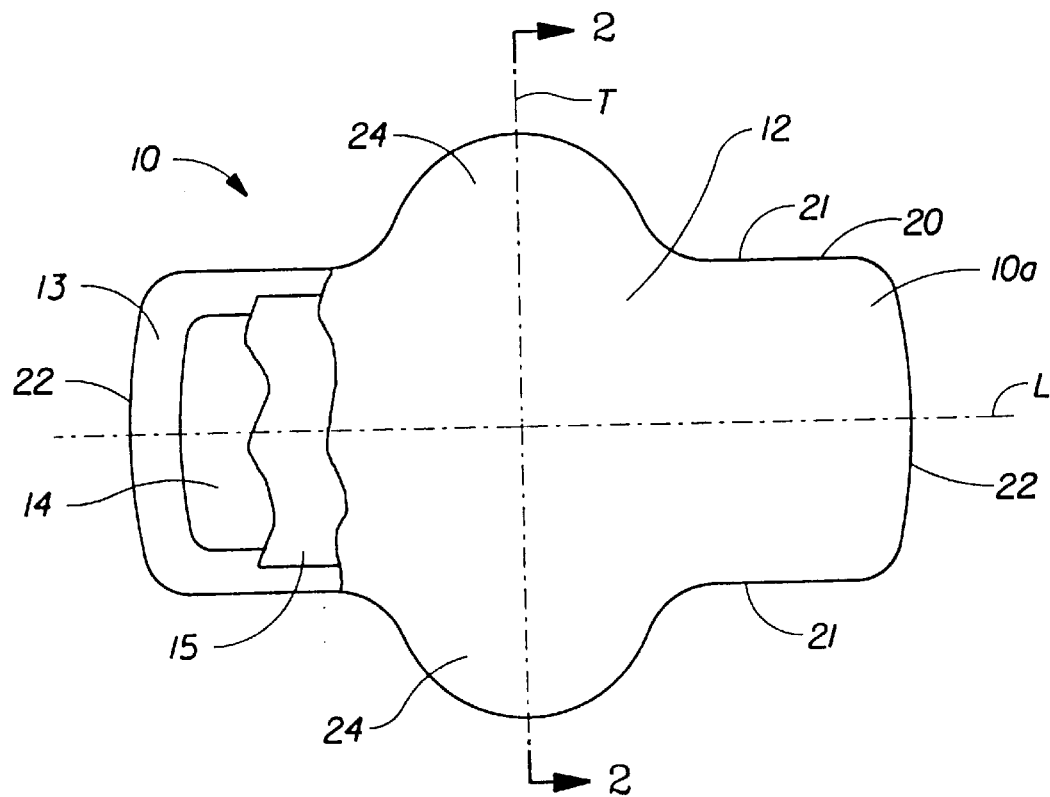
FIG. 1 is a top plan view of a sanitary napkin with portions of the sanitary napkin cut away to more clearly show the construction of the sanitary napkin.

As used herein, the term "in-use wet tensile strength" means the tensile strength of a fibrous structure, as measured using an electronic tensile tester as described in the Test Methods section, after a sample of the structure has been soaked in 5% sodium sulfate solution for 2 minutes at 23° C.

As used herein, the term "disposal wet tensile" means the tensile strength of a fibrous structure, as measured using an electronic tensile tester as described in the Test Methods section, after a sample of the structure has been soaked in excess distilled water for 15 seconds at 23° C.

II. Flushable Fibrous Structures

The present invention relates to flushable fibrous structures having an in-use wet tensile strength of at least about 100 g/in., preferably at least about 200 g/in., and more preferably at least about 300 g/in. In addition, the structures have a disposal wet tensile strength of not more than about 30 g/in., preferably not more than about 25 g/in. Tensile strengths are measured according to the procedures set forth in the Test Method section below. Preferred materials for preparing these flushable fibrous structures are described in detail below. In general, these preferred structures comprise fibers and a binder material, where the binder material comprises a polymer and a salt.

A. Binder Composition

In one preferred embodiment of the present invention, the binder component of the fibrous structures comprises a salt and the condensation product of polyvinyl alcohol (hereafter referred to as "PVA") and one or more substituted or unsubstituted $C_1$–$C_8$ aldehydes. This condensation product is a polyvinyl alcohol-co-acetal (referred to herein as a "PVAA").

Polyvinyl alcohols useful in making the PVAA for this preferred binder as well known in the textile and paper arts, and are available commercially from a variety of sources. These alcohols are manufactured by first polymerizing vinyl acetate, followed by hydrolysis of the acetate groups to alcohol groups. The commercial grades of PVA vary in degree of polymerization (i.e., molecular weight) and degree of hydrolysis (i.e., the number of acetate groups that are converted to hydroxyl groups). For example, commercial grades of PVA are available having a degree of hydrolysis of about 88% to those having a degree of hydrolysis in excess of 99%.

Preferred functionalized polymers useful in the present invention are those where the PVA material to be acetalized has a degree of hydrolysis of at least about 95%, more preferably at least about 97%, still more preferably at least about 98% and most preferably at least about 99%. In addition, preferred functionalized polymers are those where at least about 8% of the hydroxyl groups of the starting PVA are acetalized. More preferably, the PVAA will have from about 8 to about 20% of the starting PVA's hydroxyls acetalized, more preferably from about 10 to about 16%.

To be particularly useful in the present invention, the PVA should be acetalized to such a degree that the cloud point of the PVAA (as determined turbidimetrically by measuring a change in light transmittance) is higher than the temperature of tap water (i.e. greater than about 25° C.) and is depressed by the addition of salts. In addition, in order for the PVAA to be conveniently synthesized, it is useful that its cloud point be at least about 1° C. above the condensation reaction temperature, preferably from about 3 to about 5° C. above the condensation reaction temperature. This is to facilitate homogeneous reaction conditions during formation of the PVAA.

The skilled artisan will recognize that the level of acetalization of the starting PVA to arrive at a PVAA functionalized polymer that will provide the desired in-use wet strength is related to the degree of hydrolysis of the starting PVA, the molecular weight of the starting PVA, the aldehyde starting material, etc. In general, with other things being constant, the degree of acetalization needed increases as the degree of hydrolysis of the PVA starting material increases. Also, with other things being constant, as the molecular weight of the PVA starting material increases, the in-use wet tensile strength increases. The determination of the degree of acetalization of a given starting PVA to reach the desired in-use wet tensile strength is a matter of routine experimentation for the skilled artisan and will be dictated in part by the end-use of the product, as is discussed below.

Preferably, the PVA starting material will have an average molecular weight of at least about 80 kg/mol, more preferably at least about 160 kg/mol. In general, the higher the average molecular weight of the polymer, the greater the in-use wet strength of the corresponding fibrous substrate comprising the binder. The skilled artisan will recognize that the molecular weight of the starting PVA effects its viscosity (higher molecular weight provides higher viscosity PVA), and that lower viscosity PVA will be easier to process into the desired PVAA. However, this does not limit the scope of the invention to the use of "low" molecular weight PVAAs.

As indicated, to obtain the preferred PVAA material, the PVA starting material is reacted with a substituted or unsubstituted $C_2$–$C_8$ aldehyde, or a mixture of two or more such aldehydes. Where the aldehyde is substituted, suitable substituents include, for example, $C_1$–$C_3$ alkyl and aryl. Preferably, the aldehyde is an unsubstituted, saturated straight chain. Also preferred is where the aldehyde has from 2 to 5 carbon atoms, more preferably from 3 to 4 carbon atoms. Specific non-limiting examples of aldehydes particularly suitable for reaction with the PVA starting material are acetaldehyde, propionaldehyde, butyraldehyde, and mixtures thereof. Particularly preferred is where the aldehyde is propionaldehyde and/or butyraldehyde, most preferably butyaldehyde.

In general, the PVAA materials useful herein can be prepared by reacting a commercial grade of PVA (e.g., Airvol 350® or Airvol 165®, available from Air Products, Allentown, Pa.) and aldehyde in an aqueous solution at a temperature of about 20° C. and at a pH of approximately 2. Representative examples for preparing PVAA's useful herein are set forth below in Section VI.

Another preferred class of polymer useful in the binder component of the fibrous structures are homopolymers and copolymers derived from acrylamide monomers. These polymers have a structure according to the following general formula (I)

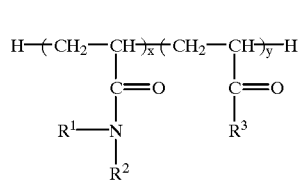

(I)

wherein
(a) x is $\geq 1$;
(b) y is $\geq 0$;
(c) $R^1$ and $R^2$ are independently selected from hydrogen and $C_1$–$C_6$ alkyl (preferably at least one of $R^1$ and $R^2$ is other than hydrogen, more preferably $R^1$ is hydrogen and $R^2$ is $C_1$–$C_3$ alkyl, still more preferably $R^1$ is hydrogen and $R^2$ is methyl, ethyl, isopropyl or n-propyl); and
(d) when y is $\geq 1$ ;
  (i) $R^3$ is —N($R^4$)($R^5$), where $R^4$ and $R^5$ are independently selected from hydrogen, $C_1C_6$ alkyl and aryl (preferably $R^4$ is hydrogen or $C_{1-C_4}$ alkyl and $R^5$ is $C_1$–$C_4$ alkyl, more preferably $R^4$ is hydrogen or $C_3$–$C_4$ alkyl and $R^5$ is $C_3$–$C_4$ alkyl); or
  (ii) $R^3$ is —O—($CH_2$—)$_z$—N($R^6$)($R^7$), where z is from 2 to about 4 (preferably 2 or 3, most preferably 2) and $R^6$ and $R^7$ are independently selected from hydrogen, $C_1$–$C_6$ alkyl, and aryl (preferably $R^6$ is hydrogen or $C_1$–$C_3$ alkyl and $R^7$ is $C_1$–$C_3$ alkyl, more preferably $R^6$ and $C_1$–$C_3$ alkyl and $R^7$ is $C_1$–$C_3$ alkyl).

In those instances where $R^6$ and $R^7$ are both alkyl groups, the resulting tertiary amine will be cationic at neutral pH and the polymer will therefore be readily adsorbed to cellulose, owing to ionic bonding with the anionic carboxyl groups of cellulose. As such, polymers of this class may be added to the wet-end of the paper making process, rather than as a separate step after substrate formation. Preferably, the polyacrylamide polymer or copolymer will have an average molecular weight of at least about 50 kg/mol, more preferably at least about 100 kg/mol, still more preferably at least about 200 kg/mol.

In general, the homo- and co-polymers derived from acrylamides are prepared by free radical polymerization following a method similar to that described in Macromolecules 1992, 25, 5353–5361, which is incorporated by reference herein. In order to obtain high molecular weight polymer, however, it is necessary to replace dioxane with t-butanol as the solvent. Representative examples for preparing polyacryolamide homo- and co-polymers useful herein are set forth below in Section VI.

In addition to the polymer, the binder component of the present invention comprises an appropriate salt that prevents the swelling and/or dissolution of the polymer in the presence of relatively small levels of water or aqueous based fluids, such as is encountered when used as tissue products or components in absorbent articles. It is this ability to resist swelling in the presence of low eater levels that provides in-use wet strength to the fibrous structures of the present invention. Salts useful herein include those comprising monovalent cations (e.g., $Li^+$, $Na^+$, $K^+$), divalent cations (e.g., $Mg^{+2}$, $Ca^{+2}$), and trivalent cations (e.g., $Al^{+3}$). Preferred are salts comprising monovalent or divalent cations. Preferred salts comprise anions such as citrate, sulfate, chloride, fluoride, bromide, thiosulfate, phosphate, nitrate, acetate, carbonate, and bicarbonate. Preferred salts include, but are ot limited to, sodium citrate, potassium citrate, sodium sulfate, potassium sulfate, magnesium sulfate, calcium sulfate, sodium phosphate, potassium phosphate, and magnesium chloride. Particularly preferred salts include potassium citrate and sodium sulfate.

Because the level of salt utilized directly effects the in-use wet strength of the binder, the level of salt required for a given fibrous structure of the present invention will be dictated in part by the end-use of the product comprising the fibrous structure. That is, where relatively low in-use wet tensile is required, such as for toilet tissue, relatively low levels of salt may be required. Conversely, where high in-use wet tensile is required, such as for a topsheet in an absorbent article, relatively higher salt levels may be utilized.

B. Fibers

The binder composition is useful for imparting temporary wet strength to a wide variety of paper and paper products. As used herein, the terms "paper" and "paper products" include sheet-like masses and molded products containing fibrous materials which may be derived from natural sources, such as wood pulp fibers, or which are synthetically derived.

Fibers of diverse natural origin are applicable to the invention. Digested cellulose fibers from softwood (derived from coniferous trees), hardwood (derived from deciduous trees or cotton linters may be utilized. Fibers from Esparto grass, bagasse, kemp, flax, and other lignaceous and cellulose fiber sources may also be utilized as raw material in the invention. For reasons of cost, ease of manufacture and disposability, preferred fibers are those derived from wood pulp (i.e., cellulose fibers). When cellulose fibers are employed, the optimum source will depend upon the particular end-use contemplated. Generally wood pulps will be utilized. Applicable wood pulps include chemical pulps, such as Kraft (i.e., sulfate) and sulfite pulps, as well as mechanical pulps including, for example, groundwood, thermomechanical pulp (i.e., TMP) and chemithermomechanical pulp (i.e., CTMP). Completely bleached, partially bleached and unbleached fibers are useful herein. It may frequently be desired to utilize bleached pulp for its superior brightness and consumer appeal. For products such as paper tissue, paper towels and substrates for diapers, sanitary napkins, catamenials, and other similar absorbent paper products, it is especially preferred to utilize fibers form northern softwood pulp due to its premium strength characteristics.

Also useful in the present invention are fibers derived from recycled paper, which can contain any or all of the above categories as well as other non-fibrous materials such as fillers and adhesives used to facilitate the original paper making process.

The fibrous structures of the present invention may comprise or consist essentially of non-cellulose fibrous material, for example, glass fibers and synthetic polymeric fibers. Synthetic polymeric fibers useful herein include polyolefins, particularly polyethylenes, polypropylene and copolymers having at least one olefinic constituent. Other materials such as polyesters, polyamides, nylons, rayons, copolymers thereof and combinations of any of the foregoing may be suitable as the fibrous polymeric material.

C. Preparing Fibrous Structures

The fibrous structures of the present invention comprise the temporary wet strength binder (polymer and salt) in combination with fibers. The polymer is combined with the fibers in a manner which, after addition of the salt, leads to a bonded fiber mass, generally in the form of a sheet containing the fibers. The bonded fiber mass has an in-use wet strength that is higher than a corresponding fiber mass without the binder.

The fibrous structures of the present invention may be prepared in a variety of ways. One important aspect, however, is that the polymer and the salt should be added to the fibers separately. That is, while the polymer and salt may be added simultaneously, they should not be admixed prior to introduction to the fibers. This is dictated by the salt's ability to precipitate the polymer if the two are combined prior to addition to the fibers.

The fibrous structures are typically formed by a wet-laid paper making process. Wet laid paper making processes typically include the steps of providing a slurry containing the fibers (the slurry is alternatively referred to herein as a paper making furnish), depositing the slurry of fibers on a substrate such as a foraminous forming wire (e.g., a Fourdrinier wire), and setting the fibers into a sheeted form while the fibers are in a substantially unflocculated condition. The step of setting the fibers into sheeted form may be performed by allowing the fluid to drain and pressing the fibers against the foraminous wire (dewatering), for example, with a screened roll, such as a cylindrical Dandy Roll. Once set, the fibrous sheet may then be dried and optionally compacted as desired.

In general, the polymer is combined with the fibers by contacting the fibers with the polymer in an aqueous liquid medium and substantially removing the medium from the fibers. The polymer may be combined with the fibers in the wet-end of the paper making process (e.g., by addition to the paper furnish) or after the paper product is substantially formed (i.e., via dry-end addition). In a preferred embodiment, the polymer and the salt are combined with the fibers after the paper product is substantially formed, e.g., by spraying or printing.

Thus, treatment of the paper or paper products with the polymer may involve spraying, printing or otherwise applying the polymer to the fibers that have been substantially set in the preparation of the paper product, e.g., by a wet laid process. The set fibers are preferably sprayed or printed with the polymer in the form of a composition which comprises a liquid solution of the polymer. Water is the preferred solvent. The liquid mixture typically contains from about 1 to about 10 weight % of the polymer and from about 90 to about 99 weight % of the solvent; for example, a mixture of about 5 weight % of the polymer and about 95 weight % of the solvent, is suitable. Optionally, a plasticizer may be included in the solution to aid in providing softness and flexibility ot the bound fibrous structure. In a preferred embodiment, the polymer solution is sprayed onto the previously set fibers. Upon drying, the salt component is added (e.g., spraying) to the fiber/polymer substrate.

As indicated, the polymer may alternatively be combined with the cellulose fibers in the wet-end of a wet-laid papermaking process. Thus, the polymer may suitably be included in the paper-making furnish. The polymer may be directly added to the furnish and agitated to cause its dissolution. Alternatively, a solution of the polymer is first prepared and then added to the furnish. In either case, depending on the nature of the polymer, it may be necessary to introduce a positive charge into the polymer so that is can readily adsorb to the anionic cellulose fibers when added to the wet-end of the paper making process. For example, a small amount of 4-dimethylaminobutyraldehyde dimethylacetal may be added along with the unsubstituted $C_2$ to $C_4$ aldehyde while making PVAA to provide the positive charge. Alternative to supplying a positive charge is to heat the polymer/fiber mixture to facilitate retention of the polymer onto the fibers of the furnish. In those embodiments where the polymer of the binder is cationic under the conditions for combining the polymer and fibers, the issue of incompatibility with the fibers may be obviated. Where the polymer is combined with the fibers via wet-end addition, the salt solution will preferably be added after the fiber/polymer blend has dried.

Regardless of whether the polymer is combined with the fibers via dry-end or wet-end addition, the salt may be added concurrently with (though separately) or sequentially from polymer addition. In one embodiment, the polymer and fibers are combined and the formed sheet is allowed to dry. A salt solution is then added to provide a fibrous structure of the present invention.

The polymer is advantageously used in the form of a solution, which may be further diluted with additional solvent, or concentrated. Alternatively, the polymer can be isolated and recovered by removing the solvent, e.g., by vacuum and/or evaporation. The polymer can then later be used in a temporary wet strength composition and applied to fibers for imparting temporary wet strength thereto. Such compositions comprise the PVAA polymer, a solvent suitable for substantially dissolving the polymer (preferably in water and/or a plasticizer such as glycerol, sorbitol, etc.), and optionally other paper making additives such as are known in the art (e.g., softeners, retention aids).

In a preferred embodiment, treatment is accomplished by spraying, printing or otherwise applying the polymer to the set fibers with such a composition (more preferably spraying). Spraying tends to provide higher levels of in-use wet tensile strength relative to treatment via the wet-end in a handsheet paper making process.

The amount of polymer that is combined with the cellulose fibers is selected to provide a balance of in-use wet tensile strength, disposal wet tensile strength, and optionally other properties, including dry strength, consistent with the objects of the invention. The paper products will typically contain from about from about 0.5 weight % to about 20 weight %, preferably from about 1 weight % to about 15 weight %, more preferably from about 1 weight % to about 10 weight % of the polymer, based on the total weight of the fibrous structure. The wet strength properties of the fibrous structure will depend on its end-use (e.g., a tissue product or a component of an absorbent article).

The composition comprising the polymer is allowed to remain in contact with the fibers for a time and at a temperature sufficient to enable adsorption of the polymer by the fibers and bonding between the polymer and fibers such that significant wet strength is developed via the bond formation (interfiber bonds are formed). When the fibers are treated by spray application on conventional commercial paper making equipment, the production time, e.g. the paper air-drying time (conventionally less than 4 minutes), may need to be increased to enable significant levels of wet strength to develop.

The fibers and the polymer may be combined at any pH, though it may be desirable to avoid strongly acid conditions that might lead to acid catalyzed hydrolysis of the polymer.

The paper product that is being treated with the polymer is preferably subjected to a drying step to remove water and/or any other solvents so as to develop the in-use wet strength. Drying may be accomplished by subjecting the paper product to elevated temperatures, e.g., in the range of from about 85° C. to about 125° C., for a time sufficient to achieve the desired level of dryness, typically to constant weight.

The present invention is particularly adapted for paper products, or components of paper products, which are to be disposed into seer systems. Accordingly, it is to be understood that the present invention is applicable to a variety of paper products including, but not limited to, disposable absorbent paper products such as those used for household, body, or other cleaning applications. Exemplary paper products thus include tissue paper including toilet tissue and facial tissue, paper towels, core materials for absorbent articles such as feminine hygiene articles including sanitary napkins, pantiliners and tampons, diapers, adult incontinent articles and the like, and topsheet and/or backsheet materials for such absorbent articles.

III. Absorbent Articles

As used herein, the term "absorbent article" refers generally to devices sued to absorb and contain body exudates, and more specifically refers to devices which are placed against or in proximity to the body of the wearer to absorb and contain the various exudates discharged from the body. The term "absorbent article" is intended to include diapers, catamenial pads, tampons, sanitary napkins, incontinent pads, and the like, as well as bandages and wound dressings. The term "disposable" is used herein to describe absorbent articles which are not intended to be laundered or otherwise restored or reused as an absorbent article (i.e., they are intended to be discarded after limited use, and, preferably, to be recycled, composted or otherwise disposed of in an environmentally compatible manner). A "unitary" absorbent article refers to absorbent articles which are formed as a single structure or as separate parts united together to form a coordinated entity so that they do not require separate manipulative parts such as a separate holder and pad.

A preferred embodiment of a unitary disposable absorbent article made in accordance herewith is the sanitary napkin 10, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention. It should be understood, however, that the present invention is also applicable to other feminine hygiene or catamenial pads, or other absorbent articles such as diapers, incontinent pads, and the like, as well as other webs designed to facilitate fluid transport away from a surface such as disposable towels, facial tissues, and the like.

It is to be understood that the overall size, shape, and/or configuration of the absorbent article, if any, into which fluid transport webs according to the present invention are incorporated, or utilized in conjunction with, have no criticality or functional relationship to the principles of the present invention. Such parameters, however, must be considered along with the intended fluid and intended functionality when determining appropriate web configurations.

Sanitary napkin 10 is illustrated as having two surfaces, first surface 10a, sometimes referred to as a wearer-contacting or facing surface, a body-contacting or facing surface or "body surface", and second surface 10b, sometimes referred to as a garment-facing or contacting surface, or "garment surface". The sanitary napkin 10 is shown in FIG. 1 as viewed from its first surface 10a. The first surface 10a is intended to be worn adjacent to the body of the wearer. The second surface 10b of the sanitary napkin 10 (shown in FIG. 2) is on the opposite side and is intended to be placed adjacent to the wearer's undergarment when the sanitary napkin 10 is worn.

The sanitary napkin 10 has two centerlines, a longitudinal centerline "L" and a transverse centerline "T". The term "longitudinal", as used herein, refers to a line, axis or direction in the plane of the sanitary napkin 10 that is generally aligned with (e.g., approximately parallel to) a vertical plane which bisects a standing wearer into left and right body halves when the sanitary napkin 10 is worn. The terms "transverse" or "lateral" as used herein, are interchangeable and refer to a line, axis or direction which lies within the plane of the sanitary napkin 10 that it generally perpendicular to the longitudinal direction. FIG. 1 also shows that the sanitary napkin 10 has a periphery 20 which is defined by the outer edges of the sanitary napkin 10 in which the longitudinal edges (or "side edges") are designated 21 and the end edges (or "ends") are designated 22.

FIG. 1 is top plan view of a sanitary napkin 10 of the present invention in a substantially flat state with portions of the sanitary napkin being cut away to more clearly show the construction of the sanitary napkin 10 and with the portion of the sanitary napkin 10 which faces or contacts the wearer 10a oriented towards the viewer. As shown in FIG. 1, the sanitary napkin 10 comprises a liquid pervious topsheet 12 which is a fibrous structure of the present invention, a liquid impervious backsheet 13 joined with the topsheet 12, an absorbent core 14 positioned between the topsheet 12 and the backsheet 13, and a secondary topsheet or acquisition layer 15 positioned between the topsheet 12 and the absorbent core 14. To facilitate flushability of the entire napkin, it is preferred that the other components of the article also be comprised of flushable materials.

The sanitary napkin 10 preferably includes optional side flaps or "wings" 24 that are folded around the crotch portion of the wearer's panty. The side flaps 24 can serve a number of purposes, including, but not limited to helping to hold the napkin in proper position while protecting the wearer's panty from soiling and keeping the sanitary napkin secured to the wearer's panty.

Figure 2:
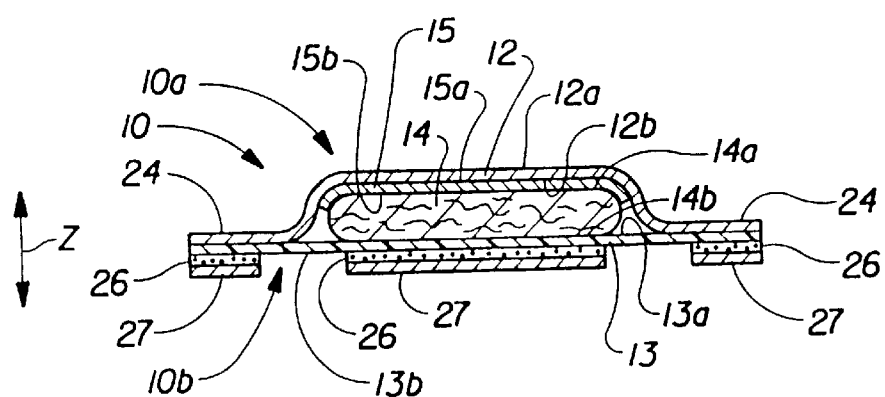
FIG. 2 is a cross-sectional view of the sanitary napkin of FIG. 1 taken along section line 2—2.

FIG. 2 is a cross-sectional view of the sanitary napkin 10 taken along section line 2—2 of FIG. 1. As can be seen in FIG. 2, the sanitary napkin 10 preferably includes an adhesive fastening means 26 for attaching the sanitary napkin 10 to the undergarment of the wearer. Removable release liners 27 cover the adhesive fastening means 26 to keep the adhesive from sticking to a surface other than the crotch portion of the undergarment prior to use.

The topsheet 12 has a first surface 12a and a second surface 12b positioned adjacent to and preferably secured to a first surface 15a of the fluid acquisition layer 15 to promote fluid transport from the topsheet to the acquisition layer. The second surface 15b of the acquisition layer 15 is positioned adjacent to and is preferably secured to the first surface 14a of an absorbent core or fluid storage layer 14 to promote fluid transport from the acquisition layer to the absorbent core. The second surface 14b of the absorbent core 14 is positioned adjacent to and is preferably secured to the first surface 13a of the backsheet 13.

In addition to having a longitudinal direction and a transverse direction, the sanitary napkin 10 also has a "Z" direction or axis, which is the direction proceeding downwardly through the topsheet 12 and into whatever fluid storage layer or core 14 that may be provided. The objective is to provide a substantially continuous path between the topsheet 12 and the underlying layer or layers of the absorbent article herein, such that fluid is drawn in the "Z" direction and away from the topsheet of the article and toward its ultimate storage layer.

The absorbent core 14 may be any absorbent means which is capable of absorbing or retaining liquids (e.g., menses and/or urine), and preferably is flushable. As shown in FIGS. 1 and 2, the absorbent core 14 has a body surface 14a, a garment facing surface 14b, side edges, and end edges. The absorbent core 14 may be manufactured in a wide variety of sizes and shapes (e.g. rectangular, oval, hourglass, dogbone, asymmetric, etc.) and from a wide variety of liquid-absorbent materials commonly used in sanitary napkins and other absorbent articles such as communitive wood pulp which is generally referred to as airfelt. Examples of other suitable absorbent materials include creped cellulose wadding; meltblown polymers including coform; chemically stiffened, modified or cross-linked cellulose fibers; synthetic fibers such as crimped polyester fibers; peat moss; tissue including tissue wraps and tissue laminates; absorbent foams; absorbent sponges; superabsorbent gelling materials; or any equivalent material or combination of materials, or mixtures of these. Again, it is preferred that the absorbent core consist of materials that are flushable.

The configuration and construction of the absorbent core may also be varied (e.g., the absorbent core may have varying caliper zones (e.g. profiled so as to be thicker in the center), hydrophilic gradients, superabsorbent gradients or lower density or lower average basis weight acquisition zones; or may comprise one or more layers or structures). The total absorbent capacity of the absorbent core, should, however, be compatible with the design loading and the intended use of the absorbent article. Further, the size and absorbent capacity of the absorbent core may be varied to accommodate different uses such as incontinent pads, pantiliners, regular sanitary napkins, or overnight sanitary napkins.

Exemplary absorbent structures for use as the absorbent core in the present invention are described in U.S. Pat. No. 4,556,146 issued Dec. 3, 1985 to Swanson et al.; U.S. Pat. No. B1 4,589,876 (original patent granted May 20, 1986) reexamination issued to Van Tilburg; Apr. 27, 1993; U.S. Pat. No. 4,687,478 issued Aug. 18, 1987 to Van Tilburg; U.S. Pat. No. 5,009,653 issued Apr. 23, 1991 to Osborn; U.S. Pat. No. 5,267,992 issued Dec. 7, 1993 to Van Tilburg; U.S. Pat. No. 5,389,094 issued Feb. 14, 1995 to Lavash et al.; U.S.

Pat. No. 5,460,623 issued Oct. 24, 1995 to Emenaker et al.; U.S. Pat. No. 5,489,283 issued Feb. 6, 1996 to Van Tilburg; U.S. Pat. No. 5,569,231 issued Oct. 29, 1996 to Emenaker et al.; U.S. Pat. No. 5,620,430 issued Apr. 15, 1997 to Bamber; U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European patent Application No. 0 198 683, the Procter & Gamble Company, published Oct. 22, 1986 in the name Duenk, et al. The disclosure of each of these documents is incorporated herein by reference.

The backsheet 13 and the fibrous topsheet 12 are positioned adjacent the garment facing surface and the body facing surface respectively of the absorbent core 14 and are preferably joined thereto and to each other by attachment means (not shown) such as those well known in the art. For example, the backsheet 13 and/or the topsheet 12 may be secured to the absorbent core or to each other by a uniform continuous layer of adhesive, a patterned layer of adhesive or any array of separate lines, spirals or spots of adhesive. Adhesives which have been found to be satisfactory are manufactured by H.B. Fuller Company of St. Paul, Minn. under the designation HL-1258, and by Findlay of Minneapolis, Minn., under the designation H-2031. The attachment means will preferably comprise an open pattern network of filaments of adhesive as disclosed in U.S. Pat. No. 4,573,986 issued to Minetola et al. on Mar. 4, 1986, the disclosure of which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978 and U.S. Pat. No. 4,842,666 issued to Werenicz on Jun. 27, 1989. The disclosures of each of these patents are incorporated herein by reference. Alternatively, the attachment means may comprise heat bonds, pressure bonds, ultrasonic bonds, dynamic mechanical bonds or any other suitable attachment means or combinations of these attachment means as are known in the art.

The backsheet 13 is impervious to liquids (e.g., menses and/or urine) and is preferably manufactured from a thin film that is flushable, although other flexible liquid impervious materials may also be used. As used herein, the term "flexible" refers to materials which are compliant and are more readily conformed to the general shape and contours of the human body. The backsheet 13 prevents the exudates absorbed and contained in the absorbent core from wetting articles which contact the sanitary napkin 10 such as pants, pajamas and undergarments. The backsheet 13 may thus comprise a woven or nonwoven material, films, or composite materials such as a film-coated nonwoven material. Preferably, the backsheet of the polyethylene film having a thickness of from about 0.012 mm (0.5 mil) to about 0.051 mm (2.0 mil). Further, the backsheet 13 may permit vapors to escape from the absorbent core 14 (i.e., breathable) while still preventing exudates from passing through the backsheet 13.

In use, the sanitary napkin 10 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer or garment facing surface 13b of the backsheet 13 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation 2238. Suitable adhesive fasteners are also described in U.S. Pat. No. 4,917,697. Before the sanitary napkin is placed in use, the pressure-sensitive adhesive is typically covered with a removable release liner 27 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, Wis. The sanitary napkin 10 of the present invention is used by removing the release liner and thereafter placing the sanitary napkin in a panty so that the adhesive contacts the party. The adhesive maintains the sanitary napkin in its position within the panty during use.

In a preferred embodiment of the present invention, the sanitary napkin has two flaps 24 each of which are adjacent to and extend laterally from the side edge of the absorbent core. The flaps 24 are configured to drape over the edges of the wearer's panties in the crotch region so that the flaps are disposed between the edges of the wearer's panties and the thighs. The flaps serve at least two purposes. First, the flap help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; and U.S. Pat. No. 4,589,876 entitled "Sanitary Napkin", which issued to Van Tilburg on May 20, 1986. The disclosure of each of these patents is hereby incorporated herein by reference.

In a preferred embodiment of the present invention, an acquisition layer(s) 15 may be positioned between the topsheet 12 and the absorbent core 14. The acquisition layer 15 may serve several functions including improving wicking of exudates over and into the absorbent core. There are several reasons why the improved wicking of exudates is important, including providing a more even distribution of the exudates throughout the absorbent core and allowing the sanitary napkin 10 to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. The disclosures of each of these references are hereby incorporated herein by reference In a preferred embodiment, the acquisition layer may be joined with the topsheet by any of the conventional means for joining webs together, most preferably by fusion bonds as is more fully described in the above-referenced Cree application.

IV. Wet Strength Properties

With regard to paper tissue, the temporary wet strength polymers of the present invention can be used in any type of tissue paper construction. For example, tissue paper of the present invention can be homogeneous or multi-layered construction; and tissue paper products made therefrom can be of a single-ply or multi-ply construction. The tissue paper preferably has a basis weight of between about 10 g/m² and about 65 g/m², and a density of about 0.6 g/cm³ or less. More preferably, the basis weight will be about 40 g/m² or less and the density will be about 0.3 g/cm³ or less. Most preferably, the density will be between about 0.04 g/cm³ and about 0.2 g/cm³. See Column 13, lines 61–67, of U.S. Pat. No. 5,059,282 (Ampulski et al), issued Oct. 22, 1991, which describes how the density of tissue paper is measured and is incorporated by reference herein. (Unless otherwise specified, all amounts and weights relative to the paper are on a dry basis.) The tissue paper may be conventionally pressed tissue paper, pattern densified tissue paper, and uncompacted, nonpattern-densified tissue paper. These types of tissue paper and methods for making such paper are well known in the art and are described, for example, in U.S. Pat. No. 5,334,286, issued on Aug. 2, 1994 to D. Phan et al., incorporated herein by reference in its entirety.

Fibrous structures formed with the temporary wet strength binder of the present invention tend to have a high in-use wet tensile strength and a wet strength decay rate suitable for flushability without a significant risk of sewer system clogging under normal use conditions. The aforementioned tensile properties may be determined as described in the following experimental section.

V. Test Method Section—Wet Strength Tests

The fibrous structures are aged prior to tensile testing a minimum of 24 hours in a conditioned room where the temperature is 73° F.±4° F. (22.8° C.±2.2° C.) and the relative humidity is 50%±10%. Both the in-use and disposal wet strength tests are performed on one in. by five in. (about 2.5 cm×12.7 cm) strips of test material in a conditioned room where the temperature is 73° F.±4° F. (about 22.8° C.±2.2° C.) and the relative humidity is 50%±10%. An electronic tensile tester (Model 1122, Instron Corp.) is used and operated at a crosshead speed of 0.5 in. (about 1.3 cm) per minute and a gauge length of 1.0 in. (about 2.5 cm). The two ends of the test strip are placed in the jaws of the machine and the center of the strip is placed around a stainless steel peg. Reference to a machine direction means that the sample being tested is prepared such that the 5 in. dimension corresponds to that direction. Thus, for a machine direction (MD) wet tensile strength, the strips are cut such that the 5 in. dimension is parallel to the machine direction of manufacture of the fibrous structure. For a cross machine direction (CD) wet tensile strength, the strips are cut such that the 5 in. dimension is parallel to the cross-machine direction of manufacture of the fibrous structure. Machine-direction and cross-machine directions of manufacture are well known terms in the art of paper-making.

The MD and CD wet tensile strengths are determined using the above equipment and calculations in the conventional manner. The reported value for the MD and CD wet tensile strengths is the arithmetic average of at least eight strips tested for each directional strength. The wet tensile strength is the arithmetic total of the MD and CD tensile strengths. When laboratory handsheets are used, 5 in. lengths are cut irrespective of orientation. The wet tensile strength (In-use or Disposal) is the arithmetic average of the wet strength measured on at least eight strips.

a. In-Use Wet Tensile Strength

In-Use Wet Tensile Strength is measured by soaking the test strip in 5% sodium sulfate solution for 2 minutes at 23° C., and then measuring tensile strength per the above description. This measurement is believed to reflect the conditions a fibrous structure of the present invention would encounter when used as a tissue product or as a component in an article for absorbing aqueous fluids.

b. Disposal Wet Tensile Strength

Disposal Wet Tensile Strength is measured by soaking a test sample in distilled water for 15 seconds at 23° C., followed by measure per the above description. This measurement is believed to reflect the conditions a fibrous structure of the present invention would encounter when disposed of in a typical sewage system.

The following non-limiting examples are provided to illustrate the present invention. The scope of the invention is to be determined by the claims which follow.

VI. Representative and Comparative Examples a. Representative Examples

Example 1

Preparation of a PVAA and a Fibrous Structure Prepared Using the PVAA

This example illustrates the preparation of a PVAA polymer useful in the binder composition for the fibrous structures of the present invention. The starting PVA has a degree of hydrolysis of approximately 99%.

2.0 grams of polyvinyl alcohol (catalog #6, lot #6 from Scientific Polymer Products; degree of hydrolysis and approximate number average molecular weight of 99% and 86 Kg/mol, respectively) are added to 100 grams of deionized water in a clean 250 mL beaker. The beaker is heated gradually with stirring until the polymer is dissolved. The solution is cooled, and 1 drop of concentrated $H_2SO_4$ pre-diluted in 10 mL of deionized water is added. Then 0.68 g propanal (as received from Aldrich chemical) are added. The beaker is covered and the mixture is stirred for 22 hours at 23° C. The solution exhibits a cloud point of 32° C. A hand-held airbrush-type sprayer is used to spray this solution onto machine-made paper having a basis weight and wet tensile strength of 33 g/m² and <15 g/in., respectively. The treated paper is dried at 23° C. to constant weight. The amount of polymer added is 5%, based on the weight of the dry untreated paper. In-use and disposal wet tensiles for the treated paper are 284 g/in. and <15 g/in., respectively. In this example, the salt component of the binder composition is introduced via the 5% sodium sulfate solution required by the in-use wet tensile strength testing protocol. That is, the salt component is not added prior to testing. (It will be recognized that addition of salt prior to testing would provide even higher in-use wet tensile strengths.) However, it is understood that in most instances (e.g., commercial uses or applications), the salt component will be added during manufacture, and in particular after addition of the polymer component of the binder, to provide a fibrous structure of the present invention. In this regard, for purposes of determining whether or not a fibrous structure is within the scope of the accompanying claims, the structure will be tested according to the Test Methods in the form that it is made, used and/or sold (i.e., if any salt is present in the structure, it will not be removed prior to measuring in-use or disposal wet tensile strengths).

Example 2

Preparation of a PVAA and a Fibrous Structure Prepared Using the PVAA

This example illustrates the preparation of another PVAA useful in the binder composition for the fibrous structures of the present invention. The starting PVA has a degree of hydrolysis of approximately 98–98.8%.

Northern Softwood Kraft (NSK) Pulp (available as Grand Prairie® fibers from Weyerhauser, Inc., Federal Way, Wash.) fibers are dispersed in water and collected on a Fourdrinier wire using a deckle box. The fibers are dewatered and dried. The resulting paper handsheets have good uniformity and a basis weight of 37 g/m$^2$. Ten grams of Airvol 350 (Air Products, Inc., Allentown, Pa.) are added to 490 g deionized water in a clean 1000 mL beaker and heated gradually with stirring to 95° C. and held for 20 minutes. The solution is cooled, and 1N $H_2SO_4$ is used to bring the pH to 2.0. Then 2.15 mL butanal (as received from Aldrich chemical ) are added. The beaker is covered and the mixture is stirred for 15 hours at 21–23° C. The pH is adjusted to 7.0–7.5 with NaOH. The solution exhibits a cloud point of 25.0° C. Proton NMR results indicate that the degree of acetalization is 15.5%. A hand-held airbrush-type sprayer is used to spray this solution onto the hand-made paper described above. The sample is dried in a convection oven at 60° C. to constant weight. The amount of polymer added is 8%, based on the weight of the dry untreated paper. In-use and disposal tensiles are 290 g/in. and 11 g/in., respectively. As with Example 1, the salt component of the binder composition is introduced to the fibrous structure of this example via the 5% sodium sulfate solution required by the in-use test method protocol.

Example 3

Preparation of Poly(N-isopropylacrylamide)

The example illustrates the preparation of a polyacrylamide of formula (I) (y=0) useful in the binder composition for the fibrous structures of the present invention.

Into a 1 liter round bottom flask is added N-isopropylacrylamide (50.03 g, 0.442 mole), 2,2'-azobis-2-methylpropionitrile (hereafter "AIBN") (0.3636 g, 0.00221 moles) and t-butanol (250 mL). After the solution is homogenous, oxygen is removed by three successive freeze-pump-thaw cycles. At the end of the third cycle, the solution is left under positive argon pressure and placed in a 70° C. oil bath. After maintaining the reaction at this temperature for 16 hours, it is cooled and the contents of the flask are transferred with water to dialysis bags (molecular weight cut off 12,000 to 14,000). After dialyzing against water, the contents of the bags are frozen and poly(N-isopropylacrylamide) is collected by freeze drying. A fibrous structure comprising poly(N-isopropylacrylamide) in the binder composition is prepared in accordance with the procedure described in Example 2. A solution of poly(N-isoproprylacrylamide) (1.0% by weight in water, exhibiting a cloud point of 32° C.) is sprayed (10 mL) onto a 12 in. by 12 in. NSK handsheet with a basis weight of 16.5 pounds per 3000 square feet (made according to the process described in Example 2). After allowing sufficient time for the water to evaporate (16 hours), the handsheet is sprayed (5.0 mL) with a 0.6 M aqueous solution of sodium sulfate to afford a fibrous structure with an in-use wet tensile of greater than 100 g/in. and a disposal tensile of less than 30 g/in.

Example 4

Preparation of Poly(N-isopropylacrylamide-co-t-butylacrylamide)

The example illustrates the preparation of a polyacrylamide copolymer of formula (I) (y≧1) useful in the binder composition for the fibrous structures of the present invention.

Into a 50 mL round bottom flask is added N-isopropylacrylamide (3.592 g, 31.7 mmoles), t-butylacrylamide (0.446 g, 3.5 mmoles), AIBN (0.0309 g, 0.188 mmoles) and t-butanol (20 mL). After the solution is homogenous, oxygen is removed by three successive freeze-pump-thaw cycles. At the end of the third cycle, the solution is left under positive argon pressure and placed in a 60° C. oil bath. After maintaining the reaction at this temperature for 16 hours, it is cooled and the contents of the flask are transferred to dialysis bags (molecular weight cut off 12,000 to 14,000). After dialyzing against water, the contents of the bags are frozen and poly(N-isoproylacrylamide-co-butylacrylamide) is collected as a white solid by freeze drying. A fibrous structure comprising poly(N-isopropylacrylamide-co-t-butylacrylamide) in the binder composition is prepared in accordance with the procedure described in Example 3. The fibrous structure has an in-use wet tensile of greater than 100 g/in. and a disposal tensile of less than 30 g/in.

Example 5

Preparation of Poly(N-isopropylacrylamide-co-dimethylaminoethyl acrylate)

This example illustrates the preparation of another polyacrylamide copolymer of formula (I) (y≧1) useful in the binder composition for the fibrous structures of the present invention. This copolymer has cationic character to which facilitates adsortion to cellulosic fibers.

Into a 100 mL round bottom flask is added N-isopropylacrylamide (9.431 g, 83.3 mmoles), N,N-dimethylaminoethyl acrylate (0.03708 g, 2.59 mmoles), AIBN (0.0711 g, 0.433 mmoles) and t-butanol (50 mL). After the solution is homogenous, oxygen is removed by three successive freeze-pump-thaw cycles. At the end of the third cycle the solution is left under positive argon pressure and placed in a 60° C. oil bath. After maintaining the reaction at this temperature for 16 hours, it is cooled and the contents of the flask transferred to dialysis bags (molecular weight cut off 12,000 to 14,000). After dialyzing against water the contents of the bags are frozen and poly(N-isopropylacrylamide-co-dimethylaminoethyl acrylate) is collected by freeze drying. A fibrous structure comprising poly(N-isopropylacrylamide-co-dimethylaminoethyl acrylate) in the binder composition is prepared in accordance with the procedure described in Example 2. Because poly(N-isopropylacrylamide-co-dimethylaminoethyl acrylate) is cationic, it can be added to the NSK furnish during handsheet preparation. Consequently the resulting handsheet already contains the polymer, and can be sprayed (5.0 mL) directly with 0.6M sodium sulfate to produce a fibrous structure with an in-use wet tensile of greater than 100 g/in. and a disposal tensile of less than 30 g/in.

b. Comparative Example

Comparative Example A

(PVAB from partially hydrolyzed PVOH)

This Comparative example demonstrates the low in-use tensile strength of a structure formed using a PVAA formed from a PVA having a relatively low degree of hydrolysis.

Northern Softwood Kraft Pulp (Grand Prairie®) fibers were dispersed in water and collected on a Fourdrinier wire using a deckle box. The fibers were dewatered and dried. The resulting paper handsheets had good uniformity and a basis weight of 37 g/m². Ten (10) g of Airvol 540 (Air Products, Inc.) (degree of hydrolysis of approximately 88%) were added to 490 grams of deionized water in a clean 1000 mL beaker and heated gradually with stirring to 95° C. and held for 20 minutes. The solution was cooled, and 1N $H_2SO_4$ was used to bring the pH to 2.0. (Approximately 1.65 mL butanal (as received from Aldrich chemical) were added.) The beaker was covered and the mixture was stirred for 22 hours at 21–23° C. The solution had a cloud point lower than ambient temperature. The polymer was collected and dissolved in slightly acidified dimethylsulfoxide (DMSO) at 60° C., then was cooled. This solution was sprayed onto the hand-made paper. The sample was dried in a convection oven at 60° C. to constant weight. The amount of polymer added was 13% based on the weight of the dry untreated paper. In-use and disposal tensiles were 46 g/in. and 8 g/in., respectively.

Comparative Examples B Through F

Northern Softwood Kraft Pulp (Grand Prairie®) fibers were dispersed in water and collected on a Fourdrinier wire using a deckle box. The fibers were dewatered and dried. The resulting paper handsheets had good uniformity and a basis weight of 37 grams/m². Each polymer described in Tables 1 and 2 below was obtained from the commercial source shown, and dissolved in water to give a 2 w/w % solution. Each solution was sprayed onto the hand-made paper. The samples were dried to constant weight at 60° C. in a convection oven. The amount of polymer added to the paper, based on the weight of the dry untreated paper is shown (ranging from 6–9%).

TABLE 1

Polymers shown in Comparative Examples B through F

| Code | Polymer | Trade Name | Commercial Source |
|---|---|---|---|
| B | Polyethyl Ozaxoline | Aquazol 200 | Polymer Chemistry Innovations, Tucson, AZ |
| C | Hydroxy Propyl Cellulose | Klucel | Aqualon Co. Wilmington, DE |
| D | Poly(vinyl methyl ether) | — | Scientific Polymer Products Ontario, NY |
| E | PVOH 70 15080-104A | — | Air Products, Allentown, PA |
| F | PVOH 78 15267 | — | Air Products, Allentown, PA |

TABLE 2

Attributes of and results from Comparative Examples B through F

| Code | Mn (kg/mol) | Mw (kg/mol) | Cloud Point (° C.) | Polymer amount (%) | In-use Tensile | Disposal Tensile |
|---|---|---|---|---|---|---|
| B | 200 | — | 75 | 7 | 13 | 10 |
| C | — | — | 35 | 7 | 13 | 10 |
| D | 130 | 200 | 30–35 | 6 | 15 | 12 |
| E | 44–65 | — | ~30 | 9 | 19 | 15 |
| F | 70–100 | — | 45–55 | 9 | 18 | 10 |

Clearly, these polymers do not provide the combined in-use and disposal tensiles that are obtained with the fibrous structures of the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A flushable fibrous structure having an in-use wet tensile strength of at least about 100 g/in. and a disposable wet tensile strength of not more than about 30 g/in. wherein said flushable fibrous structure comprises fibers, a salt, and a polymer.

2. The flushable fibrous structure of claim 1 wherein the polymer is the condensation product derived from reacting polyvinyl alcohol and one or more substituted or unsubstituted $C_1$–$C_8$ aldehydes.

3. The flushable fibrous structure of claim 2 wherein the polyvinyl alcohol reacted to form the polymer has a degree of hydrolysis prior to condensation of at least about 95%.

4. The flushable fibrous structure of claim 3 wherein the polyvinyl alcohol reacted to form the polymer has a degree of hydrolysis prior to condensation of at least about 97%.

5. The flushable fibrous structure of claim 4 wherein the polyvinyl alcohol reacted to form the polymer has a degree of hydrolysis prior to condensation of at least about 98%.

6. The flushable fibrous structure of claim 2 wherein the aldehyde reacted to form the polymer has from 2 to 5 carbon atoms.

7. The flushable fibrous structure of claim 6 wherein the aldehyde reacted to form the polymer is propionaldehyde, butyraldehyde, or a mixture thereof.

8. The flushable fibrous structure of claim 2 wherein the polymer is derived from the condensation of at least about 8% of the hydroxyl groups of the starting polyvinyl alcohol.

9. The flushable fibrous structure of claim 8 wherein the polymer is derived from the condensation of from about 8% to about 20% of the hydroxyl groups of the starting polyvinyl alcohol.

10. The flushable fibrous structure of claim 9 wherein the polymer is derived from the condensation of from about 10% to about 16% of the hydroxyl groups of the starting polyvinyl alcohol.

11. The flushable fibrous structure of claim 1 wherein the salt is selected from the group consisting of sodium citrate, sodium sulfate, potassium sulfate, sodium phosphate, potassium phosphate, magnesium sulfate, magnesium chloride, calcium sulfate, and mixtures thereof.

12. The flushable fibrous structure of claim 11 wherein the salt is selected from the group consisting of potassium citrate, sodium sulfate, and mixtures thereof.

13. The flushable fibrous structure of claim 1 wherein the polymer constitutes from about 0.5 weight % to about 20 weight % of the fibrous structure.

14. The flushable fibrous structure of claim 1 wherein the polymer has a structure according to formula (I)

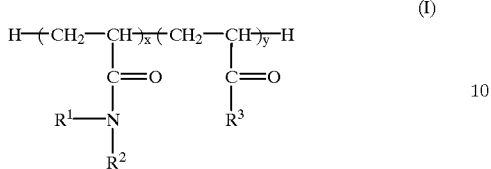

(I)

wherein
(a) x is $\geq 1$;
(b) y is $\geq 0$;
(c) $R^1$ and $R^2$ are independently selected from hydrogen and $C_1$–$C_6$ alkyl; and
(d) when y is $\geq 1$,
 (i) $R^3$ is —N($R^4$) ($R^5$), where $R^4$ and $R^5$ are independently selected from hydrogen, $C_1$–$C_6$ alkyl, and aryl; or
 (ii) $R^3$ is —O—(—CH$_2$—)$_z$—N($R^6$) ($R^7$), where z is from 2 to about 4 and $R^6$ and $R^7$ are independently selected from hydrogen $C_1$–$C_6$ alkyl, and aryl.

15. The flushable fibrous structure of claim 14 wherein y is 0; $R^1$ is hydrogen or $C_1$–$C_3$ alkyl; and $R^2$ is $C_1$–$C_3$ alkyl.

16. The flushable fibrous structure of claim 15 wherein $R^1$ is hydrogen and $R^2$ is methyl, ethyl, isopropyl, or n-propyl.

17. The flushable fibrous structure of claim 14 wherein y is $\geq 1$ and
(a) $R^3$ is —N($R^4$) ($R^5$) where $R^4$ is hydrogen or $C_1$–$C_4$ alkyl and $R^5$ is $C_1$–$C_4$ alkyl; or
(b) $R^3$ is —O—(—CH$_2$—)$_z$—N($R^6$) ($R^7$) where z is 2 or 3, $R^6$ is hydrogen or $C_1$–$C_3$ alkyl and $R^7$ is $C_1$–$C_3$ alkyl.

18. The flushable fibrous structure of claim 17 where
(a) $R^3$ is —N($R^4$) ($R^5$), where $R^4$ is hydrogen or $C_3$–$C_4$ alkyl and $R^5$ is $C_3$–$C_4$ alkyl; or
(b) $R^3$ is —O—(—CH$_2$—)$_z$—N($R^6$) ($R^7$), where $R^6$ is $C_1$–$C_3$ alkyl and $R^7$ is $C_1$–$C_3$ alkyl.

19. A flushable fibrous structure comprising fibers, a salt, and a polymer which is the condensation product derived from reacting polyvinyl alcohol and one or more substituted or unsubstituted $C_1$–$C_8$ aldehydes.

20. The flushable fibrous structure of claim 19 wherein the polyvinyl alcohol reacted to form the polymer has a degree of hydrolysis prior to condensation of at least about 95%.

21. The flushable fibrous structure of claim 20 wherein the polyvinyl alcohol reacted to form the polymer has a degree of hydrolysis prior to condensation of at least about 98%.

22. The flushable fibrous structure of claim 19 wherein the polyvinyl is derived from the condensation of at least about 8% of the hydroxyl groups of the starting polyvinyl alcohol.

23. The flushable fibrous structure of claim 22 wherein the polymer is derived from the condensation of from about 10% to about 16% of the hydroxyl groups of the starting polyvinyl alcohol.

24. A flushable fibrous structure comprising fibers, a salt, and a polymer which is the condensation product derived from reacting (i) polyvinyl alcohol having a degree of hydrolysis prior to condensation of at least about 95% and (ii) one or more substituted or unsubstituted $C_1$–$C_8$ aldehydes; wherein the polymer is derived from the condensation of from about 8% to about 20% of the hydroxyl groups of the starting polyvinyl alcohol (i).

25. A flushable fibrous structure comprising fibers, a salt, and a polymer which has a structure according to formula (I)

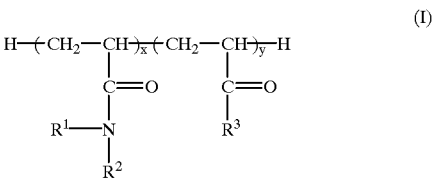

(I)

wherein
(a) x is $\geq 1$;
(b) y is $\geq 0$;
(c) $R^1$ and $R^2$ are independently selected from hydrogen and $C_1$–$C_3$ alkyl; and
(d) when y is $\geq 1$,
 (i) $R^3$ is —N($R^4$) ($R^5$), where $R^4$ and $R^5$ are independently selected from hydrogen, $C_1$–$C_6$ alkyl, and aryl; or
 (ii) $R^3$ is —O—(—CH$_2$—)$_z$—N($R^6$) ($R^7$), where z is from 2 to about 4 and $R^6$ and $R^7$ are independently selected from hydrogen $C_1$–$C_6$ alkyl, and aryl.

26. The flushable fibrous structure of claim 25 wherein y is 0; $R^1$ is hydrogen or $C_1$–$C_3$ alkyl; and $R^2$ is $C_1$–$C_3$ alkyl.

27. The flushable fibrous structure of claim 26 wherein $R^1$ is hydrogen and $R^2$ is methyl, ethyl, isopropyl, or n-propyl.

28. The flushable fibrous structure of claim 25 wherein y is $\geq 1$ and
(a) $R^3$ is —N($R^4$) ($R^5$, where $R^4$ is hydrogen or $C_1$–$C_4$ alkyl and $R^5$ is $C_1$–$C_4$ alkyl; or
(b) $R^3$ is —O—(—CH$_2$—)$_z$—N($R^6$) ($R^7$), where z is 2 or 3, $R^6$ is hydrogen or $C_1$–$C_3$ alkyl and $R^7$ is $C_1$–$C_3$ alkyl.

29. The flushable fibrous structure of claim 28 where
(a) $R^3$ is —N($R^4$) ($R^5$, where $R^4$ is hydrogen or $C_3$–$C_4$ alkyl and $R^5$ is $C_3$–$C_4$ alkyl; or
(b) $R^3$ is —O—(—CH$_2$—)$_z$—N($R^6$) ($R^7$), where $R^6$ is $C_1$–$C_3$ alkyl and $R^7$ is $C_1$–$C_3$ alkyl.

30. A disposable absorbent article comprising:
A. a liquid pervious topsheet;
B. a liquid impervious backsheet; and
C. an absorbent core positioned between the topsheet and the backsheet;
wherein the topsheet comprises the flushable fibrous structure of claim 1.

31. A disposable absorbent article comprising:
A. a liquid pervious topsheet;
B. a liquid impervious backsheet; and
C. an absorbent core positioned between the topsheet and the backsheet;
wherein the topsheet comprises the flushable fibrous structure of claim 2.

32. A disposable absorbent article comprising:
A. a liquid pervious topsheet;
B. a liquid impervious backsheet; and
C. an absorbent core positioned between the topsheet and the backsheet;
wherein the topsheet comprises the flushable fibrous structure of claim 9.

33. A disposable absorbent article comprising:
A. a liquid pervious topsheet;
B. a liquid impervious backsheet; and
C. an absorbent core positioned between the topsheet and the backsheet;

wherein the topsheet comprises the flushable fibrous structure of claim 14.

34. A disposable absorbent article comprising:

A. a liquid pervious topsheet;

B. a liquid impervious backsheet; and

C. an absorbent core positioned between the topsheet and the backsheet;

wherein the topsheet comprises the flushable fibrous structure of claim 19.

35. A disposable absorbent article comprising:

A. a liquid pervious topsheet;

B. a liquid impervious backsheet; and

C. an absorbent core positioned between the topsheet and the backsheet;

wherein the topsheet comprises the flushable fibrous structure of claim 24.

36. A disposable absorbent article comprising:

A. a liquid pervious topsheet;

B. a liquid impervious backsheet; and

C. an absorbent core positioned between the topsheet and the backsheet;

wherein the topsheet comprises the flushable fibrous structure of claim 25.

* * * * *